(12) United States Patent
Patoğlu

(10) Patent No.: US 8,366,591 B2
(45) Date of Patent: Feb. 5, 2013

(54) RECONFIGURABLE ANKLE EXOSKELETON DEVICE

(75) Inventor: Volkan Patoğlu, Istanbul (TR)

(73) Assignee: Sabanci University, Istanbul (TR)

( * ) Notice: Subject to any disclaimer, the term of this patent is extended or adjusted under 35 U.S.C. 154(b) by 101 days.

(21) Appl. No.: 12/823,054

(22) Filed: Jun. 24, 2010

(65) Prior Publication Data

US 2010/0331150 A1 Dec. 30, 2010

Related U.S. Application Data

(60) Provisional application No. 61/220,193, filed on Jun. 24, 2009, provisional application No. 61/227,033, filed on Jul. 20, 2009.

(51) Int. Cl.
*A63B 23/08* (2006.01)
*A61F 5/01* (2006.01)

(52) U.S. Cl. ................. 482/79; 482/51; 602/16

(58) Field of Classification Search .......... 482/51, 482/92, 148, 66, 79–80; 600/592, 587; 602/16, 602/27

See application file for complete search history.

(56) References Cited

U.S. PATENT DOCUMENTS

| | | | | |
|---|---|---|---|---|
| 4,605,220 A | * | 8/1986 | Troxel | 482/79 |
| 4,765,615 A | * | 8/1988 | Case | 482/116 |
| 5,215,508 A | * | 6/1993 | Bastow | 482/79 |
| 5,368,546 A | * | 11/1994 | Stark et al. | 601/34 |
| 5,393,282 A | * | 2/1995 | Maclean | 482/70 |
| 5,658,241 A | * | 8/1997 | Deharde et al. | 602/5 |
| 5,711,746 A | * | 1/1998 | Carlson | 482/112 |
| 5,987,726 A | * | 11/1999 | Akeel | 29/407.08 |
| 6,042,510 A | * | 3/2000 | Miller | 482/51 |
| 6,277,057 B1 | * | 8/2001 | Hayden | 482/79 |
| 6,581,437 B2 | * | 6/2003 | Chrystall et al. | 73/7 |
| 6,942,604 B2 | * | 9/2005 | Teff | 482/79 |
| 7,190,141 B1 | * | 3/2007 | Ashrafiuon et al. | 318/568.12 |
| 7,192,410 B1 | * | 3/2007 | Rodgers | 602/36 |
| 7,485,074 B2 | * | 2/2009 | Chen | 482/80 |
| 7,648,444 B2 | * | 1/2010 | Johnson | 482/52 |
| 7,708,669 B2 | * | 5/2010 | Rodgers, Jr. | 482/52 |
| 7,892,154 B1 | * | 2/2011 | Alexa | 482/112 |
| 7,935,027 B2 | * | 5/2011 | Graber | 482/51 |
| 2007/0129653 A1 | * | 6/2007 | Sugar et al. | 601/5 |
| 2008/0096724 A1 | * | 4/2008 | Ju et al. | 482/5 |
| 2009/0017990 A1 | * | 1/2009 | Ochi et al. | 482/6 |
| 2009/0030530 A1 | * | 1/2009 | Martin | 623/53 |
| 2009/0048074 A1 | * | 2/2009 | Kamins | 482/52 |
| 2009/0048081 A1 | * | 2/2009 | Kamins | 482/131 |
| 2009/0306548 A1 | * | 12/2009 | Bhugra et al. | 600/587 |
| 2010/0145233 A1 | * | 6/2010 | Zhang et al. | 600/592 |
| 2010/0198124 A1 | * | 8/2010 | Bhugra | 602/5 |
| 2010/0273619 A1 | * | 10/2010 | Ozawa et al. | 482/146 |
| 2011/0021956 A1 | * | 1/2011 | Shinomiya et al. | 601/5 |
| 2011/0021957 A1 | * | 1/2011 | Shinomiya et al. | 601/5 |

(Continued)

OTHER PUBLICATIONS

H. Tropp and H. Alaranta, *Sport Injuries: Basic Principles of Prevention and Care, Proprioception and coordination training in injury prevention*. Oxford, 1993.

(Continued)

*Primary Examiner* — Stephen Crow
(74) *Attorney, Agent, or Firm* — Intellectual Property Law Group LLP

(57) ABSTRACT

The present invention relates to a ungrounded, reconfigurable, parallel mechanism based, force feedback exoskeleton device for the human ankle. The primary use for the device is aimed as a balance/proprioception trainer, while the exeskeleton device can also be employed to accommodate range of motion (RoM)/strengthening exercises. This device is also used for metatarsophalangeal joint exercises.

11 Claims, 5 Drawing Sheets

U.S. PATENT DOCUMENTS

| | | | | |
|---|---|---|---|---|
| 2011/0071441 | A1* | 3/2011 | Rodgers | 601/5 |
| 2011/0105962 | A1* | 5/2011 | Ochi et al. | 601/5 |
| 2011/0105969 | A1* | 5/2011 | Nace | 602/16 |
| 2011/0167554 | A1* | 7/2011 | Sato et al. | 4/541.6 |
| 2011/0256983 | A1* | 10/2011 | Malack et al. | 482/4 |
| 2011/0306473 | A1* | 12/2011 | Saglia et al. | 482/79 |
| 2012/0004581 | A1* | 1/2012 | Dinon | 601/23 |

OTHER PUBLICATIONS

D. Hung, M. Kennedy, A. Rowland, J. D. Purdy, and M. Yampolsky, "Ankle rehabilitation: Evidence-based approach," Vanderbilt Rehabilitation Services, 2008.

J. Yoon, J. Ryu, and K. Lim, "A novel reconfigurable ankle rehabilitation robot for various exercise modes," Journal of Robotic Systems (Currently Journal of Field Robotics), 2006, vol. 22, No. 1, pp. 15-33.

R. Ekkelenkamp, P. Veltink, S. Stramigioli, and H van der Kooij, "Evaluation of a virtual model control for the selective support of gait functions using an exoskeleton," ICORR2007. IEEE 10th International Conference on Rehabilitation Robotics, Jun. 2007, pp. 693-699.

M. Girone, G. Burdea, and M. Bouzit, "The Rutgers Ankle orthopedic rehabilitation interface," in Proceedings of the ASME Haptics Symposium, vol. 67, 1999, pp. 305-312.

M. Girone, G. Burdea, and M. Bouzit, V. Popescu, and J. Deutsch, "Orthopedic rehabilitation using the Rutgers Ankle interface," in Proceedings of Virtual Reality Meets Medicine, 2000, pp. 89-95.

J. E. Deutsch, J. Latonio, G. Burdea, and R. Boian, "Rehabilitation of musculoskeletal injuries using the Rutgers ankle haptic interface: Three case reports," in Proceedings of Eurohaptics 2001, Jul. 1-4, 2001, pp. 93-98.

J. E. Deutsch, J. Latonio, G. C. Burdea, and R. Boian, "Post-stroke rehabilitation with the Rutgers ankle system: A case study,"Presence: Teleoper. Virtual Environ., 2001, vol. 10, No. 4, pp. 416-430.

M. Girone, G. Burdea, M. Bouzit, V. Popescu, and J. E. Deutsch, "A Stewart platform-based system for ankle telerehabilitation," Autonomous Robots, 2001, vol. 10, No. 2, pp. 203-212.

R. F. Boian, M. Bouzit, G. C. Burdea, J. Lewis, and J. E. Deutsch, "Dual Stewart platform mobility simulator," in Proceedings of the ICORR 2005, 9th International Conference on Rehabilitation Robotics, 2005, pp. 550-555.

J. S. Dai, T. Zhao, and C. Nester, "Sprained ankle physiotherapy based mechanism synthesis and stiffness analysis of a robotic rehabilitation device." Auton. Robots, 2004, vol. 16, No. 2, pp. 207-218.

A. Agrawal, S. Banala, S. Agrawal, and S. Binder-Macleod, "Design of a two degree-of-freedom ankle-foot orthosis for robotic rehabilitation,", ICORR 2005. 9th International Conference on Rehabilitation Robotics, Jun.-Jul. 1, 2005, pp. 41-44.

A. Roy, H. Krebs, S. Patterson, T. Judkins, I. Khanna, L. Forrester, R. Macko, and N. Hogan, "Measurement of human ankle stiffness using the Anklebot," ICORR 2007, IEEE 10th International Conference on Rehabilitation Robotics, Jun. 2007, pp. 356-363.

C. E. Syrseloudis, I. Z. Emiris, C. N. Maganaris, and T. E. Lilas, "Design framework for a simple robotic ankle evaluation and rehabilitation device," Engineering in Medicine and Biology Society, 2008. EMBS 2008. 30th Annual 15 International Conference of the IEEE, Aug. 2008, pp. 4310-4313.

J. Yoon and J. Ryu, "A new family of hybrid 4-DoF parallel mechanisms with two platforms and its application to a footpad device," Journal of Robotic Systems, 2005, vol. 22, No. 5, pp. 287-298.

Jungwon Yoon, "A novel reconfigurable ankle/foot rehabilitation robot," ICRA 2005. Proceedings of the 2005 IEEE International Conference on Robotics and Automation, Apr. 2005, pp. 2290-2295.

* cited by examiner

RECONFIGURABLE ANKLE EXOSKELETON DEVICE

CROSS REFERENCE TO RELATED APPLICATIONS

This application claims priority to provisional U.S. Application No. 61/220,193, filed on Jun. 24, 2009, and provisional U.S. Application No. 61/227,033, filed on Jul. 20, 2009, both of which are incorporated herein by reference in their entireties.

BACKGROUND OF THE INVENTION

1. Field of Invention

The present invention relates to a ungrounded, reconfigurable, parallel mechanism based, force feedback exoskeleton device for the human ankle. The primary use for the device is aimed as a balance/proprioception trainer, while the exeskeleton device can also be employed to accommodate range of motion (RoM)/strengthening exercises. This device is also used for metatarsophalangeal joint exercises.

2. Background

The aim of the rehabilitation is to recover the patient's physical, sensory and neural capabilities that were impaired due to an illness or injury. Ankle rehabilitation is commonly necessitated after sprained ankles, one of the most common injuries in sports and daily life [1]. Losses of functional ability, ability to bear weight, and joint stability at the ankle are also experienced after neurological injuries secondary to stroke and contracture deformity secondary to cerebrovascular disease. Physiotherapy exercises are indispensable to re-gain range of motion (RoM) of the joint, to help restrengthen muscles to bear weight, to promote better awareness of joint position (proprioception), to ensure neural integrity, and to recover dynamic balance.

Rehabilitation of ankle injury is generally addressed in three sequential exercise phases [2], [3]. Exercises in the early phase focus on first enabling full RoM of the joint and then strengthening ankle muscles. Once the required RoM and flexibility is achieved and the muscles become strong enough to bear partial weight without inducing pain, the intermediate phase of therapy can be initiated, focusing on enhancement of proprioception ability through use of static balance exercises. In the final phase of the therapy, more advanced dynamic balancing exercises are practiced.

Traditional rehabilitation devices used to assist physiotherapy are simple passive equipment, such as elastic bands and ankle rehabilitation pumps for strengthening and stretching exercises; wobble boards and foam rollers for proprioception and balancing exercises. RoM exercises are generally performed manually by a therapist. Even though these types of equipment are simple and fixed-cost effective, these traditional devices fall short of collecting quantitative measurements of patient progress, monitoring patient history for re-evaluation, and achieving customized, interactive treatment protocols. The therapists are required to carry physical burden of movement therapy and to provide the patient with full attention while exercising with these devices.

Nowadays rehabilitation exercises have been done by the help of the robotic devices. Assistance of repetitive and physically involved rehabilitation exercises using robotic devices not only helps eliminate the physical burden of movement therapy for the therapists, but also decreases application related costs. Moreover, robot-mediated rehabilitation therapy allows quantitative measurements of patient progress and can be used to realize customized, interactive treatment protocols.

Beneficial effects of robot assisted rehabilitation protocols have been demonstrated over conventional therapy through clinical trials in the literature [4]. Recognizing the need for robot assisted rehabilitation devices for ankle physiotherapy, several designs have been proposed to date. Girone et al. proposed a force feedback interface, named Rutgers Ankle, based on Stewart platform [5]. A virtual reality based interactive training protocol was implemented using the Rutgers ankle for orthopedic rehabilitation [6]. The system was further studied through several case studies [7], [8]. Home-based remote ankle rehabilitation was addressed in Girone et al. [9], while in Boian et al, the system was extended to a dual Stewart platform configuration to be used for gait simulation and rehabilitation [10].

Dai et al. proposed another robotic device to treat sprained ankle injuries [11]. Unlike the Stewart platform design, this device progresses just enough degrees of freedom (DoF) to cover orientation workspace of the human ankle. The kinetostatic analysis presented in this reference emphasized the importance of employing a center strut to achieve higher stiffness from to device. Agrawal et al. proposed an ankle-foot orthosis for robot assisted rehabilitation and presented the kinematic analysis and the control of the proposed mechanism [12]. Similarly, Anklebot was proposed by Roy et al. to aid recovery of the ankle function [13]. This device can also be used to measure the ankle stiffness, which is a strong biomechanical factor for locomotion.

Syrseloudis and Emiris studied the translational and rotational RoM of the human ankle and foot through human subject experiments, and concluded that a parallel tripod mechanism with an additional rotational axis in series is the most relevant kinematic design to comply with human ankle related foot kinematics [14]. Yoon and Ryu proposed a hybrid four DoF parallel mechanism based footpad device and presented the kinematic analysis of the novel device [15]. This work was extended to allow for reconfiguration of the device to support several distinct exercise modes [3], [16].

It is thus an object of the invention to provide a device which has a reconfigurable design. Its implementation is simple and the device can be built assembling commercially available parts. Due to its reconfigurability, the device allows for both range of motion RoM/strengthening exercises and balance/proprioception exercises.

SUMMARY OF THE INVENTION

According to an embodiment of the present invention, the device is capable of covering the whole complex range of the human ankle for RoM/strengthening exercises. The device can support human weight during balance/proprioception exercises. Metatarsophalangeal joint exercises are also enabled via the reconfigurable design of the base plate.

According to an embodiment of the present invention, the device can be utilized as a clinical measurement tool. Ankle joint level motions, forces, and impedances can be determined to assist diagnoses.

According to an embodiment of the present invention, the device is ergonomic, allows for whole range of motion of the human ankle. The device is light and wearable; hence, is portable. The device is inherently safe due to choice of its actuators.

According to an embodiment of the present invention, the device has higher control performance than similar devices due to its parallel kinematic structure and optimized bandwidth.

According to an embodiment of the present invention, the device supports complex motions of the foot and is not limited to a single degree of freedom as the case with many existing designs.

According to an embodiment of the present invention, the device is programmed to guide, assist, or resist the patient during physical therapy and implemented with a computer system. The levels of assistance and resistance are software adjustable. The device can also be programmed to estimate ankle joint parameters, such as ankle tone and impedance.

Aspects of the device according to present invention is related to rehabilitation robots, robot-assisted rehabilitation, physical therapy devices, force feedback exoskeletons, haptic interfaces for medical treatment, clinical measurement devices, ankle rehabilitation systems, ankle orthosis, rehabilitation devices for ankle physiotherapy, devices to assess ankle function, determination of ankle impedance.

DETAILED DESCRIPTION OF THE PREFERRED EMBODIMENTS

Figure 1:
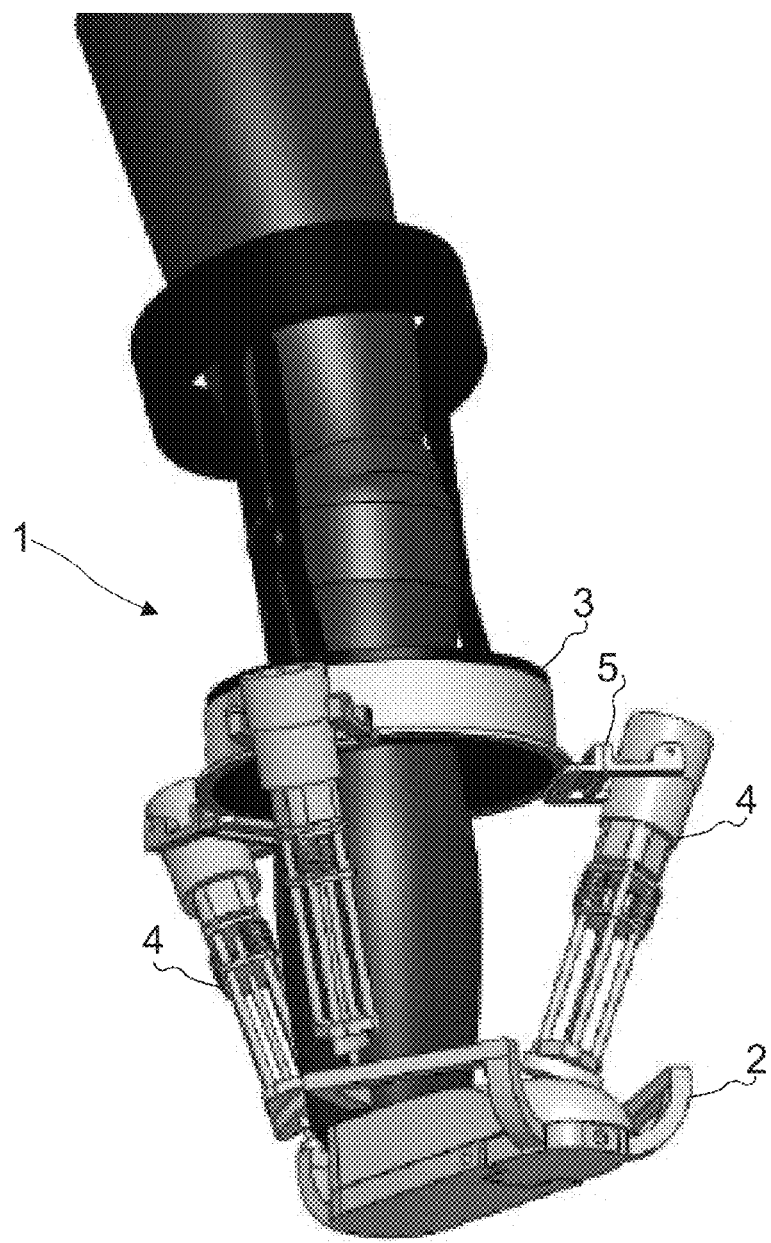
FIG. 1. is a perspective view of the device according to an embodiment of the present invention.

The following description of the preferred embodiments is merely exemplary in nature and is in no way intended to limit the invention, its application, or uses. As illustrated in FIG. 1, there is shown an ankle therapy and measurement exoskeleton device (1) according to an embodiment of the present invention, the device comprising; a moving platform (2) which faces with the foot of the operator, a base platform (3) which faces with the leg of the operator, a connecting member (4) that connects the base platform (3) and the moving platform (2).

The exoskeleton device (1) further comprises a joint member (5) which connects the connecting member (4) to the base platform (3). By the help of said joint member (5) the exoskeleton device (1) can support two different exercise types, namely RoM/Strengthening exercises and balance/proprioception exercises independently of each other. The joint member (5) can selectively be in different modes. In the preferred embodiment of the invention it switches between a universal joint and a revolute joint.

In a preferred embodiment of the invention the connecting member (4) is connected to the moving platform (2) by using spherical joints.

The ankle joint can be modeled as a spatial serial kinematic chain with two revolute joints (RR) namely an upper ankle joint and subtalar joint. The upper ankle joint supports the rotational dorsiflexion/plantarflexion motion whereas the subtalar joint supports the rotational supination/pronation motion. Supination/pronation rotation is a complex motion that has both inversion/eversion and abduction/adduction components.

The kinematic chain used in the preferred embodiment of the invention is the closed kinematic chain (parallel mechanism). Said closed kinematic chain serves as an exoskeleton and it allows for and supports the natural movements of the human joints when the device (1) is worn by the operator. A closed kinematic chain offers the compact designs with high stiffness and has low effective inertia. The actuators of the closed kinematic chains can be grounded or placed on parts of the mechanism that experiences low accelerations.

Figure 3:
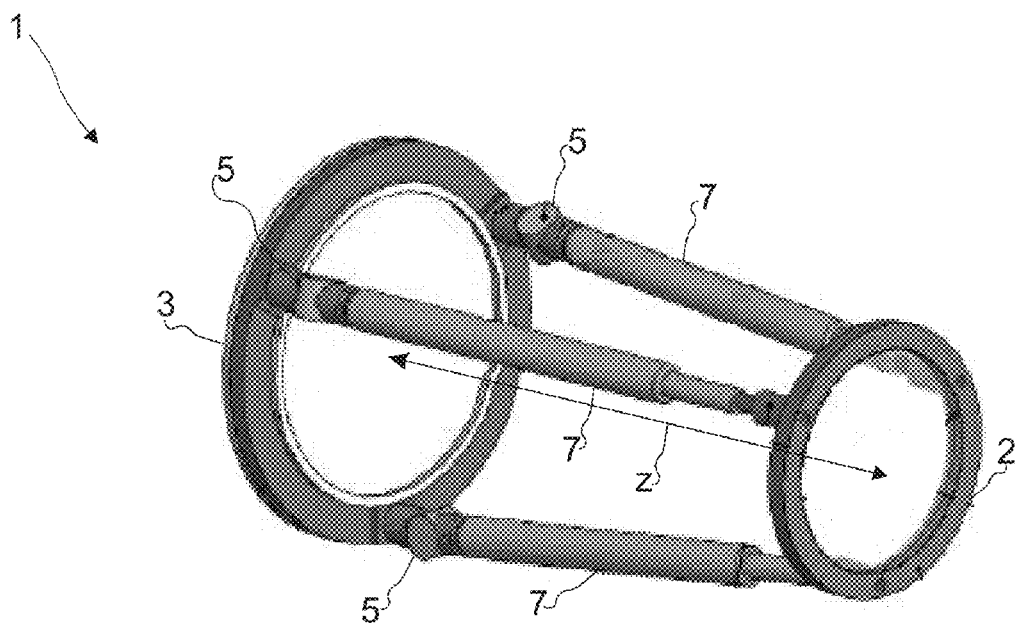
FIG. 3. is a perspective view of the device behaves as a 3RPS mechanism according to an embodiment of the present invention.
Figure 4:
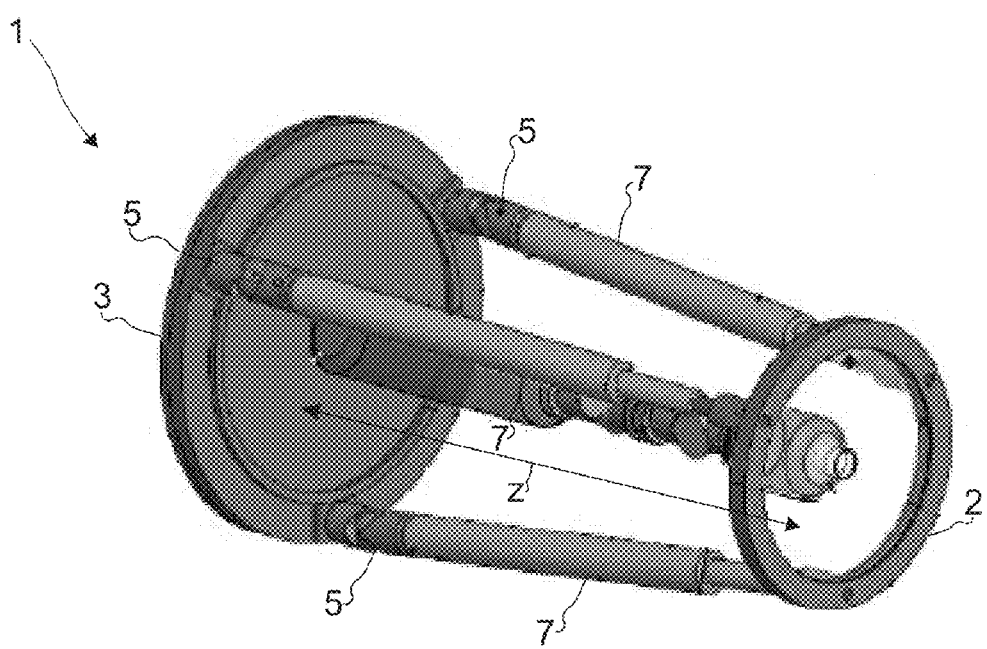
FIG. 4. is a perspective view of the device when it behaves as a 3UPS mechanism (the middle link represents the human foot and ankle) according to an embodiment of the present invention.

The closed kinematic chain used in this invention can be used as at least two different mechanisms by the help of the joint member (5). By the help of this fact, the device (1) gains a reconfigurable property. In the preferred embodiment of the invention it can be used as a 3UPS (universal, prismatic, spherical) as shown in FIG. 4, and 3RPS (revolute, prismatic, spherical) mechanisms as shown in FIG. 3, independently from each other.

Figure 5:
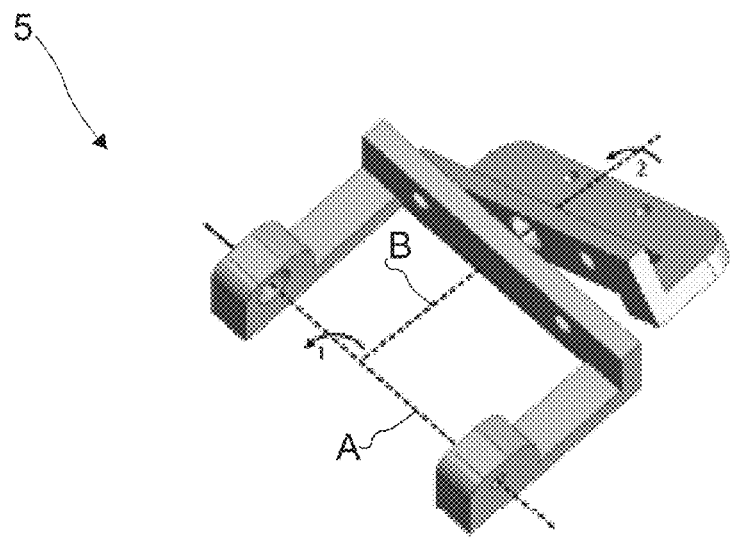
FIG. 5. is a perspective view of a joint member used in the device in unlocked position according to an embodiment of the present invention.
Figure 6:
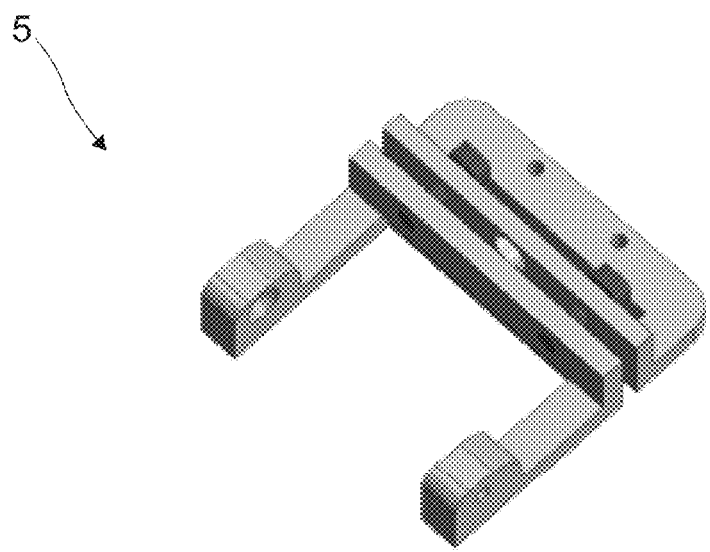
FIG. 6. is a perspective view of a joint member used in the device in locked position according to an embodiment of the present invention.

In a preferred embodiment of the invention, the joint member (5) is the reconfigurable joint which can selectively be used in unlocked or locked positions. In an unlocked position the reconfigurable joint (5) can freely rotate around two axes (A, B)(see FIG. 5). The first axis (A) is tangential to the base plate (3) while the second axis (B) is perpendicular to the base plate (3). When the joint (5) is unlocked, the series of revolute joints function as a universal joint rotating about desired said axes. When the second joint axis (B) is locked, the reconfigurable joint (5) is constrained to function as a revolute joint, that is free to rotate only around the first axis (A) (see FIG. 6). Hence, the reconfigurable joint (5) allows a 3UPS mechanism to be reconfigured into a 3RPS mechanism, and vice versa.

Figure 2:
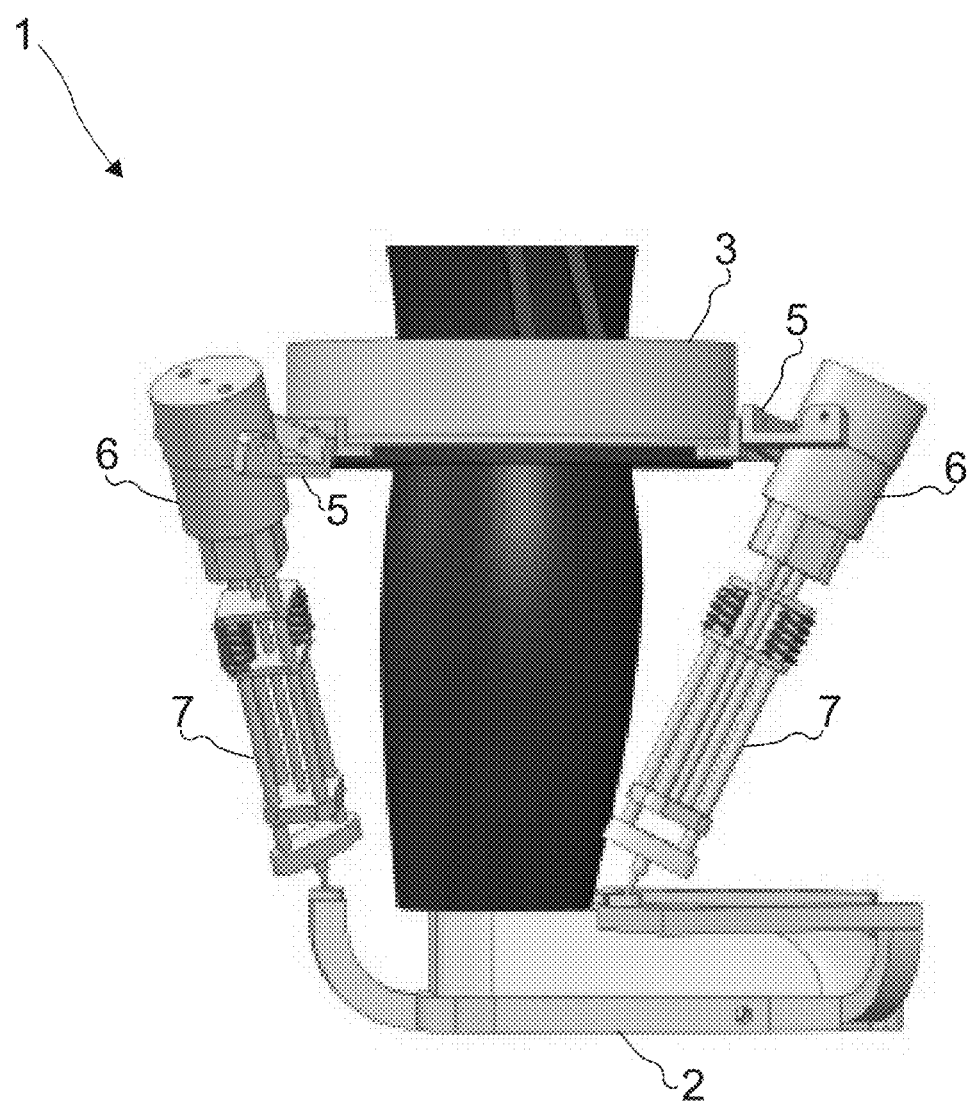
FIG. 2. is a side view of the device in 3UPS configuration according to an embodiment of the present invention.

As shown in FIGS. 1 and 2, the connecting member (4) basically comprises a drive unit (6) and a moving element (7). Drive unit (6) can apply the necessary force onto moving element (7), so that the moving element (7) can move. In a preferred embodiment of the invention the drive unit (6) is an electric motor whereas the moving element (7) is at least one extensible link.

In the case that the closed kinematic chain is used as a 3UPS mechanism, the reconfigurable joint (5) is in an unlocked position, in other words it is free to rotate about desired axes (A, B), and behaves as a universal joint. Furthermore, the leg of the operator behaves as a center links of the mechanism, in other words the operator ankle becomes a member of the mechanism. In a preferred embodiment of the invention, the mechanism is a symmetric 3UPS mechanism as shown in FIG. 4, where the universal joint (5) and the spherical joints are spaced at 120° along the circumference of the base platform (3) and the moving platform (2). When worn by the user, the 3UPS mechanism attached to the human ankle has two degrees of freedom (DoF) corresponding to a coupled motion of the moving platform (2) with respect to the fixed base platform (3). The lengths of the extensible links (7) are actuated to control these DoF. The moving platform (2) is a distance z from the base platform (3) and does not possess translational movement transverse to the vertical axis through the base (2). Even when the operator is completely passive, the two DoF 3UPS mechanism has three actuated joints; hence, is a redundant mechanism. This redundancy can be exploited to increase the effective workspace of the device (1), since singularity resolution becomes feasible in case the device (1) approaches singularities within the workspace.

In the case that the closed kinematic chain is used as a 3RPS mechanism, the reconfigurable joint (5) is in locked position, in other words the rotational motion of the joint (5) about second axis (B) is prevented. The reconfigurable joint (5) behaves as a revolute joint and its axes of rotation are oriented along the tangents of base platform (3). The base platform (3) is attached to the upper mid-calf of the leg through a passive revolute joint to allow for the internal/external rotations of the foot. In a preferred embodiment of the invention as shown in FIG. 3, the mechanism is a symmetric 3RPS mechanism where the revolute joints (5) and the spherical joints are spaced at 120° along the circumference of the base platform (3) and the moving platform (2). The 3RPS mechanism has three DoF corresponding to the height z. The lengths of the extensible links (7) are actuated to control these DoF. The moving platform (2) possesses limited translational movement transverse to the vertical axis through the base (3) and no singularities for limited values of revolute joint angles.

When the closed kinematic chain is in the 3UPS mode, the device (1) can be employed as a RoM/strengthening exercise device whereas is in the 3RPS mode it (1) can be employed as a balance/proprioception exercise device.

Couplings between the exoskeleton device (1) and the operator are designed to be elastic to ensure safety and to allow for small joint misalignments and modeling imperfections. Elasticity allows for the relative motion of the human limb with respect to the device (1) when the kinematics of the device (1) is in conflict with the natural movement of the ankle.

In one embodiment of the invention, the weight of the device (1) is distributed over the upper leg and the upper mid-calf by using tight straps around the knee.

In another embodiment of the invention the weight of the device (1) can be distributed over the body by suspending the device (1) from the shoulder of the operator.

The exoskeleton device (1) further comprises a control unit (not shown in the figures), and at least two sensors (not shown in the figures). One of the sensors measure the length of the connecting member (4) whereas the second sensor measures the axial rotation amount of the joint member (5). The measured data of the elements are processed by the control unit for calculating the configuration of the device (1) and estimating the forces acting on it (1). In particular, forward kinematics of the device (1) is used to calculate the configuration of moving platform (2), while the device (1) dynamics is used with a reaction torque observer implemented in software to estimate the forces acting on it (1).

For estimating the ankle parameters, the link (7) lengths of the kinematic chain must be known along with the rotation axes of the revolute joints. Determination of the bone lengths of the operator is relatively straightforward as x-ray images of the ankle can be studied to achieve reasonably accurate estimates. However, determination of the rotation axes is challenging since the motion of the ankle depends on the size and orientation of the foot bones, and the shape of articulated surfaces. Only course estimates of joint axes can be obtained by studying the x-ray images. More accurate estimates of joint axes are desired to study the ankle motion and such estimates are made possible thanks to the data collected with the exoskeleton.

Given good estimations of the bone lengths, the axes of rotation of the revolute joints of the human ankle can be determined by instructing the operator to perform free RoM movements and by collecting position data from the extensible links (7) and preferably three rotation sensors placed on the joint member (5). As the data becomes available, the configuration level forward kinematics of the 3UPS mechanism is solved for the moving platform (2) configurations at each instant of time. Once the foot configurations are recorded, the configuration level inverse kinematics of the two link RR manipulator with unknown the revolute joint axes (representing the human ankle) is solved for the axes of revolute joints and the amount of rotation around these axes.

Figure 7:
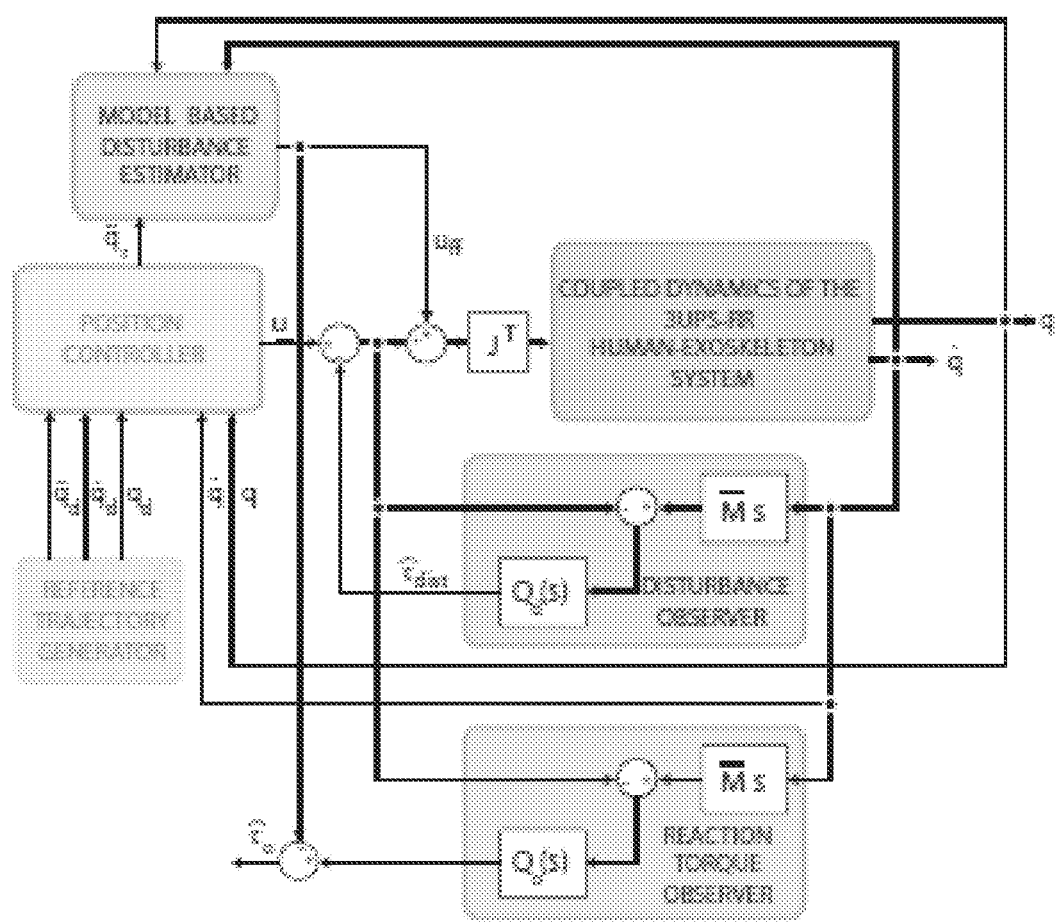
FIG. 7. is a block diagram of the robust position controller with reaction torque observer according to an embodiment of the present invention.

Given the configuration and motion level forward and inverse kinematics of the coupled 3UPS-RR system (the exoskeleton coupled to the human ankle) and the dynamic properties of the exoskeleton device (1) only, a robust position controller with a reaction torque observer can be implemented to characterize the dynamic properties of the ankle. In particular, by employing a robust position controller as that illustrated in FIG. 7, the exoskeleton device (1) can command the ankle trace a desired trajectory, while disturbance forces due to the unknown dynamics of the ankle can be estimated during this motion. In the controller implementation, forces due to the known dynamics of the exoskeleton device (1) is added to the system in a feed forward manner to ensure that the disturbance acting on the system is solely due to the unknown dynamics of the ankle. Under such a control, the forces commanded by the controller are to counteract the unmodeled dynamics of the ankle. Hence, the actuator forces can be mapped to the joint torques at the ankle and assuming that all other disturbances are comparatively small, these torques provide a close estimate of the actual joint torques provide a close estimate of the actual joint torques due to ankle dynamics.

The exoskeleton device (1) can deliver passive, active, assistive and resistive exercise modes. Virtual tunnels and force fields inside these tunnels can be implemented to enable safe practice with assistance or resistance.

Since the device (1) in 3UPS configuration allows for all possible movements of the ankle within its full range, it is possible to use the device (1) for clinical measurements. Firstly, the device can be used to determine range of motion of the patient. When the patient moves his/her ankle, the device can measure and log the time history of this movement (the trajectory). Given the measured the time history of movements, it is possible to determine how fast the patient completes a movement, the amount of error involved with respect to a reference trajectory and how smooth/intermittent these movements are. Since the kinematics of the device (1) is known, it is also possible to map the measured configuration changes to the rotations of the ankle joint. This capability allows for measurement of orientation, speed and smoothness of ankle joint movements. Coordination and synergies of joint movements can also be detected from these measurements.

As explained above, employing a robust position controller and commanding the exoskeleton device (1) to trace a desired trajectory, the disturbance forces due to the unknown dynamics of the ankle can be estimated during this motion. These forces can also be mapped to the joint torques at the ankle using ankle kinematics.

This measurement technique can be used to determine maximum joint torques the patient can exert the impedance and the tone of the patent ankle, at any configuration of the ankle. In particular, if the gains of the robust position controller is set to stay at any reference configuration, and the patient is asked to apply maximum torque at his/her ankle joints, then the disturbance forces acting on the controller can be mapped to joint torques to estimate human ankle joint torques about the relevant axes. Finally, given a pre-specified reference trajectory for the robust position controller, the joint torques can be estimated at each instant of time and the relation between the joint rotation and the joint torques can be used to estimate ankle impedance and/or tone.

In another embodiment of the invention the ungrounded, wearable and reconfigurable ankle therapy and measurement exoskeleton device can be combined with the virtual reality games.

The description of the invention is merely exemplary in nature and, thus, variations that do not depart from the gist of the invention are intended to be within the scope of the invention. Such variations are not to be regarded as a departure from the spirit and scope of the invention.

References

[1] H. Tropp and H. Alaranta, *Sport Injuries: Basic Principles of Prevention and Care, Proprioception and coordination training in injury prevention*. Oxford, 1993.

[2] D. Hung, M. Kennedy, A. Rowland, J. D. Purdy, and M. Yampolsky, "Ankle rehabilitation: Evidence-based approach," Vanderbilt Rehabilitation Services.

[3] J. Yoon, J. Ryu, and K. Lim, "A novel reconfigurable ankle rehabilitation robot for various exercise modes," *Journal of Robotic Systems (Currently Journal of Field Robotics)*, vol. 22, no. 1, pp. 15-33, 2006.

[4] R. Ekkelenkamp, P. Veltink, S. Stramigioli, and H van der Kooij, "Evaluation of a virtual model control for the selective support of gait functions using an exoskeleton," *Rehabilitation Robotics, 2007. ICORR 2007. IEEE 10th International Conference on*, pp 693-699, June 2007

[5] M. Girone, G. Burdea, and M. Bouzit, "The Rutgers Ankle orthopedic rehabilitation interface," in *Proceedings of the ASME Haptics Symposium*, vol. 67, 1999, pp. 305-312.

[6] M. Girone, G. Burdea, and M. Bouzit, V. Popescu, and J. Deutsch, "Orthopedic rehabilitation using the Rutgers Ankle interface," in *Proceedings of Virtual Reality Meets Medicine* 2000, pp. 89-95.

[7] J. E. Deutsch, J. Latonio, G. Burdea, and R. Boian, "Rehabilitation of musculoskeletal injuries using the Rutgers ankle haptic interface: Three case reports," in *Proceedings of Eurohaptics* 2001, July 1-4 2001, pp. 93-98

[8] J. E. Deutsch, J. Latonio, G. C. Burdea, and R. Boian, "Post-stroke rehabilitation with the Rutgers ankle system: A case study," *Presence: Teleoper. Virtual Environ.*, vol. 10, no. 4, pp. 416ˆ130, 2001.

[9] M. Girone, G. Burdea, M. Bouzit, V. Popescu, and J. E. Deutsch, "A Stewart platform-based system for ankle telerehabilitation," *Autonomous Robots*, vol. 10, no. 2, pp. 203-212, 2001.

[10] R. F. Boian, M. Bouzit, G. C. BURDEA, J. Lewis, and J. E. Deutsch, "Dual Stewart platform mobility simulator," in *Proceedings of the ICORR* 2005, *9th International Conference on Rehabilitation Robotics*, 2005, pp. 550-555.

[11] J. S. Dai, T. Zhao, and C. Nester, "Sprained ankle physiotherapy based mechanism synthesis and stiffness analysis of a robotic rehabilitation device." *Auton. Robots*, vol. 16, no. 2, pp. 207-218, 2004.

[12] A. Agrawal, S. Banala, S. Agrawal, and S. Binder-Macleod, "Design of a two degree-of-freedom ankle-foot orthosis for robotic rehabilitation," *Rehabilitation Robotics*, 2005. *ICORR* 2005. *9th International Conference on*, pp. 41-44, June-1 July 2005

[13] A. Roy, H. Krebs, S. Patterson, T. Judkins, I. Khanna, L. Forrester, R. Macko, and N. Hogan, "Measurement of human ankle stiffness using the Anklebot," *Rehabilitation Robotics, 2007. ICORR 2007. IEEE 10th International Conference on*, pp. 356-363, June 2007.

[14] C. E. Syrseloudis, I. Z. Emiris, C. N. Maganaris, and T. E. Lilas, "Design framework for a simple robotic ankle evaluation and rehabilitation device," *Engineering in Medicine and Biology Society*, 2008. *EMBS* 2008. *30th Annual International Conference of the IEEE*, pp. 4310-4313, Aug. 2008.

[15] J. Yoon and J. Ryu, "A new family of hybrid 4-DoF parallel mechanisms with two platforms and its application to a footpad device," *Journal of Robotic Systems, vol.* 22, no. 5, pp. 287-298, 2005.

[16] - - - , "A novel reconfigurable ankle/foot rehabilitation robot," *Robotics and Automation*, 2005. *ICRA* 2005. *Proceedings of the* 2005 *IEEE International Conference on*, pp. 2290-2295, April 2005.

What is claimed is:

1. An ungrounded, wearable and reconfigurable ankle therapy and measurement exoskeleton device comprising;
   a base platform which interfaces with a leg of an operator,
   a moving platform which interfaces with a foot of the operator, the moving platform positioned beneath the base platform,
   a connecting member that connects the base platform and the moving platform,
   a reconfigurable joint member, having a locking mechanism engaging the joint member in a locked position or an unlocked position to have more than one degree of freedom, and which connects the connecting member to the base platform;
   wherein in an unlocked position the reconfigurable joint member can freely rotate around two axes wherein a first axis is tangential to the base platform while a second axis is perpendicular to the base platform.

2. An ungrounded ankle therapy and measurement exoskeleton device according to claim 1 characterized in that the reconfigurable joint member functions as a universal joint rotating about desired said axes when in the unlocked position.

3. An ungrounded ankle therapy and measurement exoskeleton device according to claim 1 characterized in that when the reconfigurable joint member is in the locked position, the reconfigurable joint member is constrained to function as a revolute joint that is free to rotate only around the first axis.

4. An ungrounded, wearable and reconfigurable ankle therapy and measurement exoskeleton device comprising;
   a base platform which interfaces with a leg of an operator,
   a moving platform which interfaces with a foot of the operator, the moving platform positioned beneath the base platform,
   a connecting member that connects the base platform and the moving platform,
   a reconfigurable joint member, having a locking mechanism engaging the joint member in a locked position or an unlocked position to have more than one degree of freedom, and which connects the connecting member to the base platform;
   characterized in that the reconfigurable joint member allows a 3UPS mechanism in which the device is used as a RoM/strengthening exercise device to be reconfigured into a 3RPS mechanism in which the device is used as a balance/proprioception exercise device.

5. An ungrounded ankle therapy and measurement exoskeleton device according to claim 4 characterized in that when the device is used as a 3UPS mechanism, the reconfigurable joint member is in the unlocked position and behaves as a universal joint and the leg of the operator behaves as a center link of the device connecting the base platform and the moving platform.

6. An ungrounded ankle therapy and measurement exoskeleton device according to claim 4 characterized in that when the device is used as a 3RPS mechanism the reconfigurable joint member is in the locked position, and behaves as a revolute joint and its axes of rotation are oriented along the tangents of the base platform.

7. An ungrounded, wearable and reconfigurable ankle therapy and measurement exoskeleton device comprising;
   a base platform which interfaces with a leg of an operator,
   a moving platform which interfaces with a foot of the operator, the moving platform positioned beneath the base platform,
   a connecting member that connects the base platform and the moving platform,
   a reconfigurable joint member, having a locking mechanism engaging the joint member in a locked position or an unlocked position to have more than one degree of freedom, and which connects the connecting member to the base platform;
   characterized in that the connecting member comprises a drive unit and a moving element.

8. An ungrounded ankle therapy and measurement exoskeleton device according to claim 7, further comprising at least two sensors on the joint member, wherein at least one of the at least two sensors measures a length of the connecting member, and another sensor of the at least two sensors measures an axial rotation amount of the joint member; and a control unit that controls and records a plurality of movements of the moving element and processes data measured by the sensors.

9. An ungrounded ankle therapy and measurement exoskeleton device according to claim 8, characterized in that the control unit switches amongst a passive exercise mode where the device forces an ankle of the operator to move; an active exercise mode; an assistive exercise mode where the device assists a motion of the ankle; and a resistive exercise mode where the device applies resistance to the motion of the ankle.

10. An ungrounded, wearable and reconfigurable ankle therapy and measurement exoskeleton device comprising;
    a base platform which interfaces with a leg of an operator,
    a moving platform which interfaces with a foot of the operator, the moving platform positioned beneath the base platform,
    a connecting member that connects the base platform and the moving platform,
    a reconfigurable joint member, having a locking mechanism engaging the joint member in a locked position or an unlocked position to have more than one degree of freedom, and which connects the connecting member to the base platform; and
    a robust position controller measuring and observing external torques and forces, and resisting the external torques and forces by applying opposite torques and forces.

11. An ungrounded ankle therapy and measurement exoskeleton device according to claim 8 characterized in that the control unit and the at least two sensors of the device measures joint configuration, speed of movement, trajectory, trajectory error, smoothness of movement, range of motion, coordination and synergies, maximum joint torques at any configuration, joint torques while tracing any trajectory, tone and impedance of an ankle.

* * * * *